United States Patent [19]

Wilkins et al.

[11] Patent Number: 5,281,214
[45] Date of Patent: Jan. 25, 1994

[54] DISPOSABLE SURGICAL PROBE HAVING FIBER DIVERTER

[75] Inventors: Douglas P. Wilkins, Milpitas; Edmundo F. Azalde, San Jose, both of Calif.

[73] Assignee: Laserscope, San Jose, Calif.

[21] Appl. No.: 871,767

[22] Filed: Apr. 21, 1992

[51] Int. Cl.$^5$ ............................................. A61B 17/36
[52] U.S. Cl. .......................................... 606/15; 606/2; 606/13; 606/14; 606/16; 607/90; 607/93
[58] Field of Search ...................................... 606/13-17, 606/19, 2; 128/395, 398

[56] References Cited

U.S. PATENT DOCUMENTS

| | | | |
|---|---|---|---|
| 4,313,431 | 2/1982 | Frank | 606/16 |
| 4,418,688 | 12/1983 | Loeb | 606/15 |
| 4,461,283 | 7/1984 | Doi | 606/15 |
| 4,669,467 | 6/1987 | Willett et al. | 606/17 |
| 4,760,840 | 8/1988 | Fournier, Jr. et al. | 606/15 |
| 4,832,023 | 5/1989 | Murphy-Chutorian | 128/398 |
| 4,849,859 | 7/1989 | Nagasawa | 606/17 |
| 4,875,897 | 10/1989 | Lee | 606/15 |
| 4,881,524 | 11/1989 | Boebel et al. | 606/16 |
| 5,156,604 | 10/1992 | Hessel et al. | 606/15 |

FOREIGN PATENT DOCUMENTS 3840749 6/1990 Fed. Rep. of Germany ........ 606/17

OTHER PUBLICATIONS

KTP/YAG Surgical Laser System; printed by Laserscope; San Jose, Calif.

Primary Examiner—Stephen C. Pellegrino
Assistant Examiner—Jeffrey A. Schmidt
Attorney, Agent, or Firm—Mark A. Haynes

[57] ABSTRACT

A disposable fiber diverter probe is provided that eliminates many of the typical problems associated with conventional fiber diverter probes that are designed to be used multiple times and must be sterilized between each use. The present invention utilizes thermoplastic materials in many of the components that traditional designs require to be made of metal in order to perform the required functions of a fiber diverter probe. The improved design of the present invention enables less complex, low cost parts to be used in a fiber diverter probe, wherein the probe still provides expanded capabilities over conventional, more expensive fiber diverter probes, such as more accessible and user-friendly controls for the surgeon. Moreover, the reduced cost of the fiber diverter probe provided by the present invention enables a medical facility or a private physician to make disposable fiber diverter probes economically feasible, thus eliminating the risk of exposing patients to a contaminated probe.

25 Claims, 6 Drawing Sheets

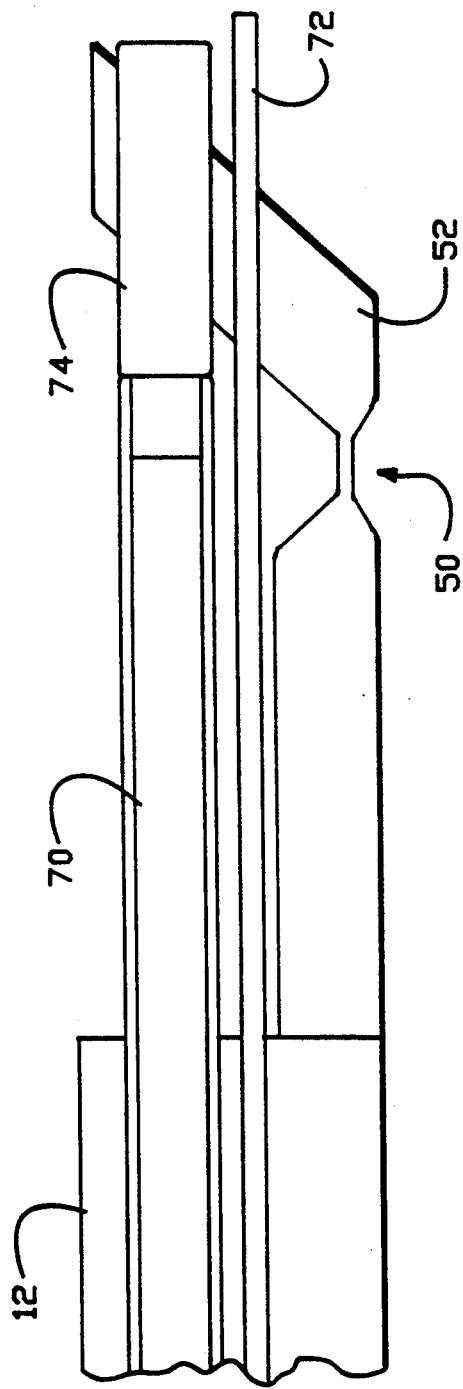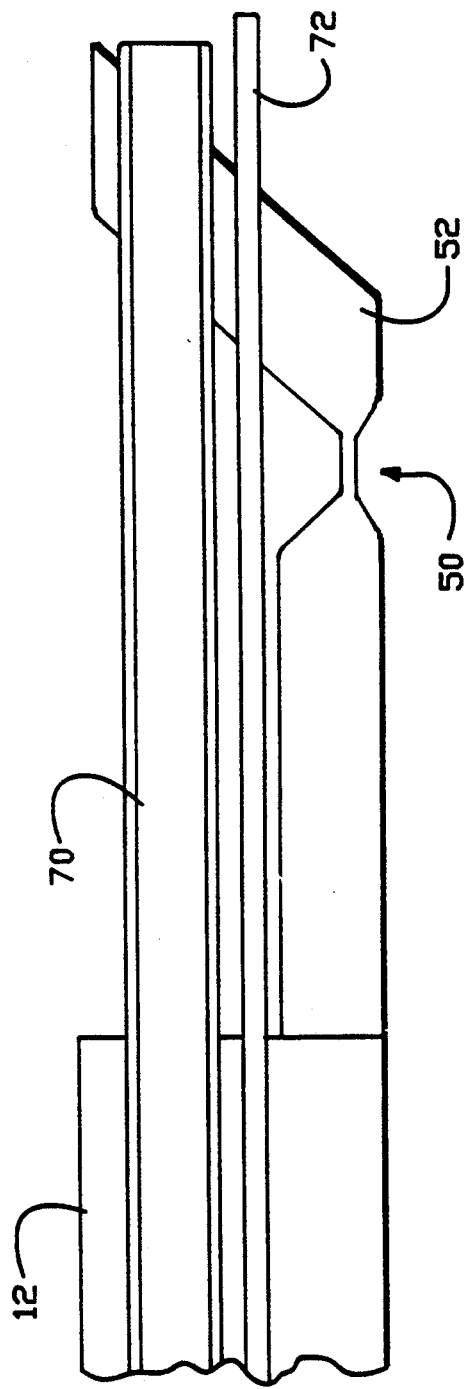

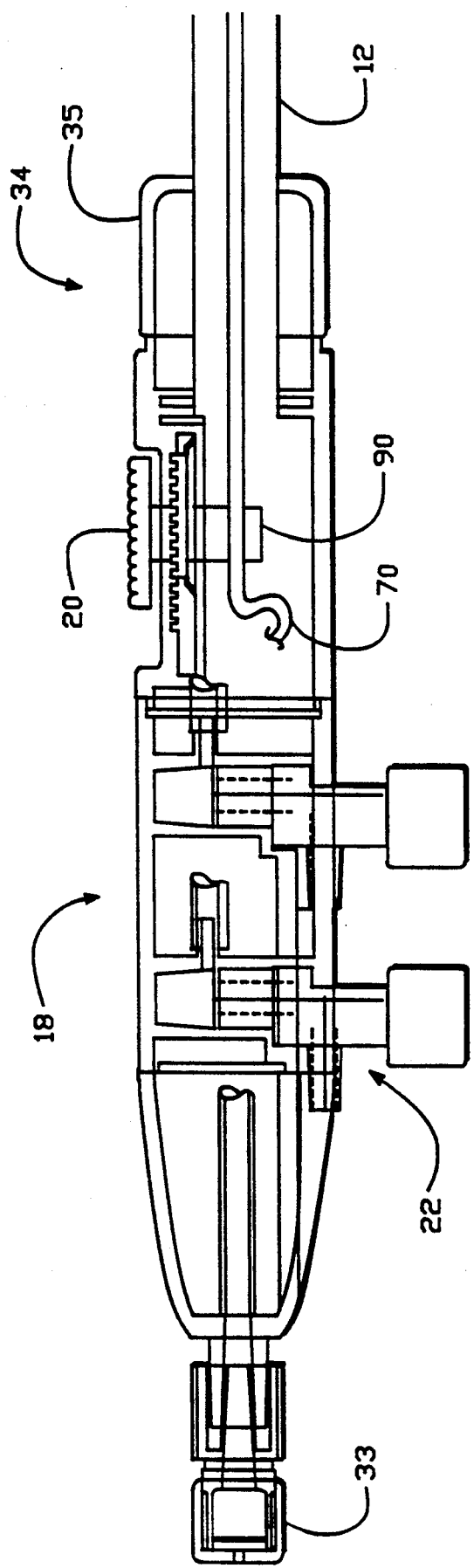
FIG.—3b

DISPOSABLE SURGICAL PROBE HAVING FIBER DIVERTER

FIELD OF THE INVENTION

The present invention relates generally to surgical laser probes, and more particularly to a disposable probe having a directional tip for aiming laser energy emitted by a tip of an optical fiber secured within the probe.

BACKGROUND OF THE INVENTION

Use of laser probes, or optical fiber delivery systems, is continuing to increase due to expanded surgical capabilities made available by improved laser probes. Modern laser probes are used in increasingly complex surgical procedures as a result of technological advancements in designs of laser probes.

Originally, a laser probe consisted basically of an optical fiber enclosed within a rigid tube that enabled a surgeon to deliver laser energy to an exact location of body tissue within a patient's body in order to precisely cut, cauterize, and/or coagulate a very small area of the body tissue. Later generations of laser probes included irrigating and aspirating capabilities that enabled surgeons to cut, cauterize, and also clean specific areas of body tissue using the same instrument, thus decreasing both trauma to a patient and complexity of a surgical operation. Modern laser probes further expand available surgical options by including a directional tip on a probe that enables a surgeon to access areas of a patient's body that may not ordinarily be accessible with a rigid linear probe.

As with most mechanical devices, however, the risk of mechanical breakdown or failure increases as the intricacy and precision of a device increases, and mechanically complex fiber diverter probes are not immune from this general rule of thumb. Even more troublesome, the intricate parts of a complex fiber diverter probe can be difficult to reach, thus making cleaning and repairing such parts also difficult.

The assignee of this application, Laserscope, presently provides a state of the art laser probe having directional, or fiber diverter, capabilities at the distal tip of the probe, in addition to simultaneous irrigating and aspirating capabilities. This complex, state of the art instrument enables surgeons not only to perform complete surgical operations on specific areas of body tissue using one instrument, but further enables surgeons to access difficult areas not readily accessible by linear, non-fiber diverter probes. Due to the complexity of such a fiber diverter probe, the device is relatively expensive to manufacture and is constructed of precisionly designed components.

Since modern fiber diverter probes are very expensive to manufacture, purchasers generally prefer that these medical instruments have an extended lifetime expectancy. Accordingly, modern fiber diverter probes are constructed of durable, heavy metal components with the intent of providing a complex medical instrument having an extended functional lifetime expectancy. For sanitary reasons, conventional probes must be able to withstand the high temperatures necessary for heat sterilization which is required between each use of the probe in order to avoid exposing patients to a contaminated medical instrument.

In actual use, however, the intricate components of these complex fiber diverter probes have been found to be very difficult to sterilize after each use. The tiny working components of the instrument can be somewhat inaccessible in sterilization procedures. Furthermore, sterilization, which usually is accomplished by exposing the instrument to high temperatures, tends to weaken, stiffen, or otherwise damage the more delicate or precision components of the fiber diverter probe.

Additional problems, that were not previously anticipated, have become apparent from the use of conventional, long-term use fiber diverter probes. For instance, the metal components of the probe create a substantial weight that can be very tiring for a surgeon who may be required to manually hold the instrument in a desired position for an extended period of time during long operations. Furthermore, conventional controls for diverting the fiber tip, such as a rotating knob, have been reported by surgeons to be difficult to use during operating procedures. Even the positioning of valves on the instrument, which regulate the flow of air or liquid during cleansing procedures, are uncomfortable for surgeons to operate.

Accordingly, it would be desireable to provide a fiber diverter probe at a relatively inexpensive price, thereby eliminating the necessity for sterilizing the instrument and making a disposable fiber diverter probe practical. In the same manner, it would also be desirable to provide a fiber diverter probe of reduced weight and user friendly controls in order to facilitate the use of fiber diverter probes by surgeons. In reducing the overall cost and weight of the instrument, it would therefore be desireable to decrease the number of separate components in the instrument. Decreasing the number of components in design of the fiber diverter probe would also provide the added advantage of reducing the risk of mechanical failures.

SUMMARY OF THE INVENTION

In view of the foregoing, the present invention provides a disposable fiber diverter probe that eliminates many of the typical problems associated with conventional fiber diverter probes which are designed to be used multiple times and must be sterilized between each use. The present invention utilizes thermoplastic materials in many of the components that traditional designs require to be made of metal in order to perform the required functions of the fiber diverter probe. The improved design of the present invention enables less complex, low cost parts to be used in a fiber diverter probe, wherein the probe still provides expanded capabilities over conventional, more expensive fiber diverter probes. Moreover, the reduced cost of the fiber diverter probe provided by the present invention enables a medical facility or a private physician to make disposable fiber diverter probes economically feasible in their practice.

As can be readily appreciated, an economically feasible, disposable fiber diverter probe completely eliminates the risk of transmitting communicable diseases to successive patients by using a probe. In a time of great paranoia of AIDS, hepatitis, and other very serious or even fatal diseases, the elimination of any risk of using a contaminated medical instrument is extremely desirable.

Briefly, the present invention provides a fiber diverter probe wherein most of the components are made of a thermoplastic material that cannot withstand temperatures or solvents necessary for sterilization procedures, and the materials will melt, deform, or decompose if exposed to heat or chemical sterilization. By constructing the probe of such materials, the possibility of a person using the probe for multiple procedures, by sterilizing the probe between uses, is essentially eliminated. This safeguard feature of the present invention provides added mental security and medical safety to both doctors and patients. Moreover, the improved design, decreases the risk of mechanical failure, decreases the weight of the probe, and decreases the cost of the probe, while still providing additional surgical capabilities over conventional fiber diverter probes.

Accordingly to one aspect, the present invention provides a fiber diverter probe wherein the control for diverting the end portion of the optical fiber within the probe is a convenient, user-friendly slidable button. The button automatically locks in position when not depressed, but slides freely when a user depresses the button. This design is more easily utilized by a surgeon during operating procedures than prior art controls, such as a rotating knob.

Moreover, trumpet valves for controlling irrigating and aspirating functions of the probe are conveniently positioned at the fingertips of a surgeon. The positioning of the trumpet valves in combination with the diverter control button enables a surgeon to operate the probe with one hand, and without having to reposition his or her hand when accessing the different controls of the probe.

According to another aspect of the present invention, a fiber diverter probe is provided wherein a fiber positioning tube of the probe is capable of rotating with respect to the probe handle. This feature enables a surgeon to vary a diverting plane of the fiber tip with respect to the probe handle and controls, thus adding another user-friendly and accessibility feature to the present invention.

In accordance with yet another feature of the present invention, a fiber diverter probe is provided having a flexible member that is slidably positioned within a hollow passage of a fiber positioning tube of the probe in order to completely eliminate the necessity for a hinge at the distal end of the probe. The distal end of the flexible member tends to form a curve when unrestricted. An optical fiber, which is positioned within a lumen of the flexible member, is thus diverted as the distal end of the flexible member is slid out of the distal end of the fiber positioning tube and is able to form a curve.

The above features and additional advantages of the present invention can be seen upon review of the figures, the detailed description, and the claims to follow.

BRIEF DESCRIPTION OF THE DRAWINGS

FIG. 3 is a cross-sectional view of an additional embodiment of the distal end of the fiber diverter probe shown in and taken along line 3—3 of FIG. 1.

FIG. 3a is a variation on the embodiment shown in FIG. 3.

FIG. 3b is a cross-sectional view of a proximal end of the probe shown in FIG. 1 that corresponds with the embodiment of FIG. 3.

DESCRIPTION OF THE PREFERRED EMBODIMENTS

Figure 1:
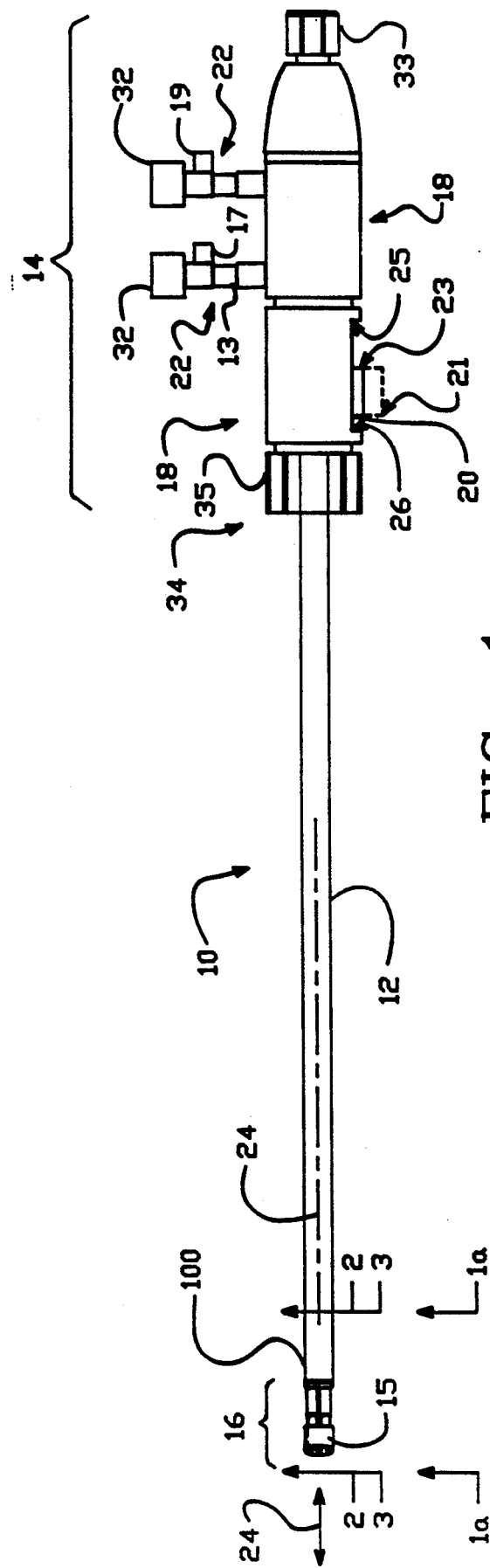
FIG. 1 is an elevational view of a fiber diverter probe configured in accordance with the present invention.

Turning now to the figures, FIG. 1 illustrates a fiber diverter probe 10 configured in accordance with the present invention. The probe 10 includes an elongated member 12 having a proximal end 14 and a distal end 100. Attached to the distal end 100 is a fiber guide 16 for deflecting the end portion of an optical fiber, the optical fiber being secured within the elongated member 12.

The elongated member 12 is constructed of substantially rigid material. For example, the elongated member 12 can be constructed of metal or "engineering thermoplastic," such as polycarbonate, polysulfane, or reinforced nylon.

The proximal end 14 of the elongated member 12 is coupled to a handle 18 having an adjustable member or adjustable button 20 and a plurality of trumpet valves 22. The adjustable button 20 slides longitudinally in a direction parallel to a longitudinal axis 24 of the elongated member 12. The button 20 is locked in position when in a non-depressed position 21 (shown in phantom), but is capable of sliding between a proximal position 25 and a distal position 26 when depressed into a depressed position 23 by a finger of an operator. The sliding motion of the button 20 controls the fiber guide which deflects the end portion of the optical fiber. The function of the fiber guide 16 will be discussed in more detail later.

While the illustrated embodiment of the elongated member 12 is shown to be linear, it is possible for elongated member 12 to be curved and still function. In such a curved embodiment, the referenced longitudinal axis 24 would also be curved accordingly to follow the elongated member 12.

The trumpet valves 22 of the handle 14 regulate flow of air and liquid in aspirating and irrigating procedures during surgery using the probe 10. The trumpet valves 22 are preferably made of a plastic material, but may be constructed of metal or other suitable materials. Irrigation and aspiration channels (FIGS. 5 and 5a) each have their own unique trumpet valve. The trumpet valves 22 allow passage through lumens (see FIG. 3b) by depressing a cap 32 on each of the valves 22.

In a preferred embodiment, the trumpet valves 22 are locked in an open position once depressed and are unlocked from the open position by squeezing or twisting the top cap 32 of a valve 22. Luer fittings 17,19 on the trumpet valves 22 enable a user to attach any standard tubing for irrigation and aspiration. Preferably, an irrigation source of pressurized fluid is to be connected to the irrigating luer 17, and an aspirating source providing suction is to be connected to the aspirating luer 19. Stems 13 of the trumpet valves 22 are both secured to the same side of the handle 18 and at angles substantially perpendicular to the longitudinal axis 24 in order to enable the valves 22 to be more easily accessible to a surgeon using one hand to operate the probe 10. Although FIG. 1 illustrates the valves 22 being on the side of the handle 18 directly opposite the button 20 for illustration purposes, the valves 22 may be preferably positioned at a side of the handle 18 approximately 90 degrees around the handle 18 from the position of the button 20.

The handle 18 also includes a fiber lock 33 for securing an optical fiber and forming a gas/liquid seal.

Rotating means or a collet mechanism 34 is included at a junction between the elongated member 12 and the handle 18. The collet mechanism 34 rotates the elongated member 12 about the longitudinal axis 24 while the handle 18 remains stationary. This feature is achieved by rotatably mounting the elongated member 12 to the handle 18, and having a collet 35 rigidly secured to the elongated member 12 (see FIG. 3b). Of course, the collet 35 and the elongated member 12 could be a unitary component.

Rotating the elongated member 12 in such a manner enables the operator manually to vary a diverting or directional plane X-Y (FIG. 1a) of the hinge 30 with respect to the adjustable button 20. This feature increases the ability of the probe 10 to access hard-to-reach areas in a patient's body while providing added comfort for the user.

Figure 1A:
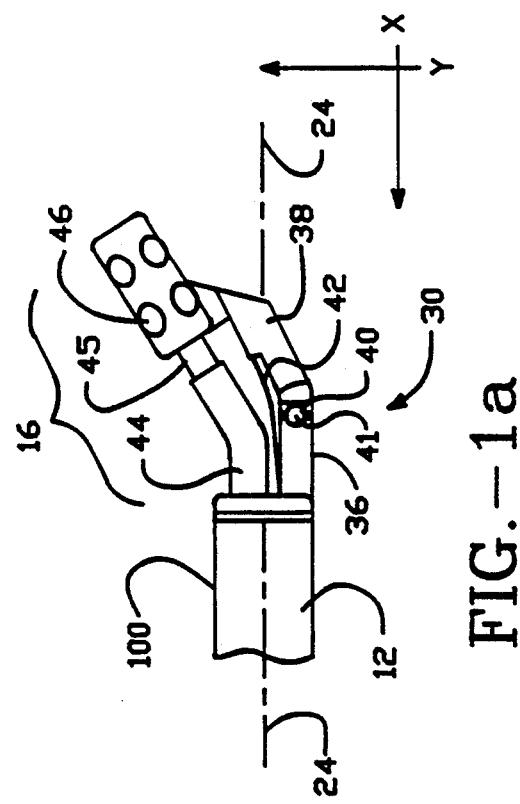
FIG. 1a is an enlarged, side view of a distal end of the probe shown in and taken along line 1a—1a of FIG. 1.

FIG. 1a illustrates an enlarged side view of one embodiment of the distal end 16 shown in FIG. 1. The illustrated pin hinge 30 is one embodiment that can be utilized for a fiber guide in the present invention. The pin hinge 30 includes a first end 36 which is secured to the elongated member 12, and a second end 38 which diverges about a joint 40. The joint 40 includes a pin 41 about which the second end 38 diverges.

A wire 42, which is connected to the adjustable button 20 and the second end 38, provides means for diverting the pin hinge 30 in response to sliding the button 20. Also illustrated in FIG. 1a is a flexible tube 44 providing an aspirating lumen. The tube 44 is secured to a tip 45 having aspirating vents 46.

In accordance with the present invention, the pin hinge 30 may be constructed of a low-cost, disposable plastic that decreases the weight of the probe 10 is addition to decreasing the cost. The disposable, one-time use, plastic pin hinge 30, while not a preferred embodiment of the present invention, does provide advantages over a conventional metal pin hinge designed for multiple uses.

For example, the precision metal pin joint in conventional metal pin hinges requires precision assembly and the metal pin hinge has been found to be affected by heat sterilization. Exposing the metal pin hinge to the high temperatures necessary for sterilization causes the precision components of the metal pin hinge to expand during heating and contract during cooling which loosens the precision joint of the metal pin hinge. Each time the metal pin hinge is exposed to sterilization procedures, the precision integrity of the conventional metal pin hinge is further compromised and the risk of mechanical failure is increased. Therefore, as disclosed below, the preferred embodiment of the present invention completely eliminates the conventional pin hinge joint design and replaces it with a low-cost, light weight, less complex component that performs the same function as a pin hinge with a lower risk of failure due to a less complex design.

Figure 2:
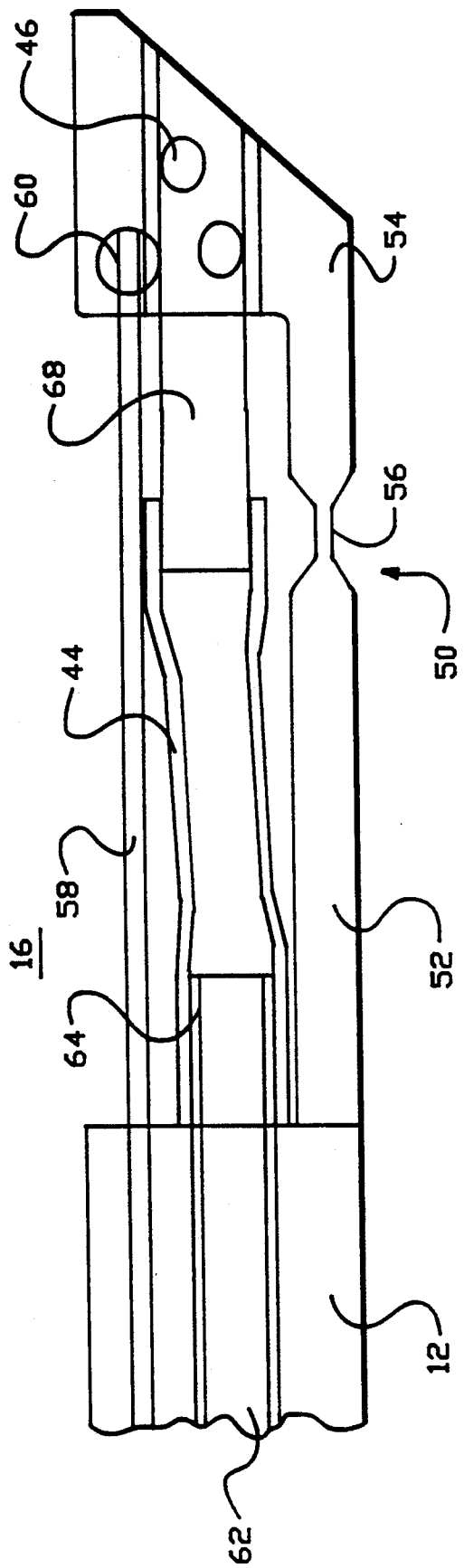
FIG. 2 is a cross-sectional view of another embodiment of the distal end of the fiber diverter probe shown in and taken along line 2—2 of FIG. 1.

In accordance with the present invention, a disposable, lightweight, less complex fiber guide is provided. Referring to FIG. 2, a cross-sectional view of one embodiment of a preferred fiber guide configured in accordance with the present invention is illustrated. This embodiment provides a "living hinge" joint 50, which is less expensive to manufacture and assemble than the pin hinge 30. The living hinge 50 is preferably a molded thermoplastic, unitary component having a first end 52 that is secured to the elongated member 12, and a second end 54 that diverts about a very thin, flexible section 56 near a midsection of the hinge 50. A plastic or metal wire 58 has one end pivotally secured to the second end 54 using a ball and socket joint 60. The wire 58, which has one end pivotally secured to the second end 54 of the hinge 50 and the other end of the wire 58 secured to the adjustable button 20 (FIG. 4), is slidably mounted within the elongated member 12 in order to diverge the second end 54 in response to sliding the adjustable button 20.

FIG. 2 also illustrates a cross-section of the aspirating lumen 62 within the elongated member 12. The aspirating lumen 62 includes an attachment port 64 for securing the flexible tube 44. Tube 44 communicates the aspirating lumen 62 with an input port 68 of the aspirating vents 46. It should be noted that lumen 62 could function as an irrigating lumen, if desired.

The living hinge 50 provides a low cost, highly functional hinge joint to be utilized on a fiber diverter probe. The improved design of the living hinge 50 reduces the risk of mechanical failure typically associated with a complex pin hinge joint. Furthermore, the low cost material of the living hinge 50, such as thermoplastic which is also easier to form into specific shapes than metal, enables the hinge 50 to be more easily manufactured and at a relatively lower cost. Moreover, the decrease in weight of the living hinge 50 as compared to a metal pin hinge joint function to further decrease the weight of the probe 10.

Each of the above aspects regarding the living hinge 50 enable a vital component of the fiber diverter probe 10 to be economically manufactured, making a highly functional, disposable fiber diverter probe feasible.

Figure 2B:
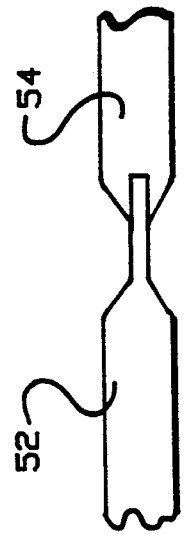
FIG. 2b is another variation of the embodiment shown in FIG. 2.
Figure 2A:
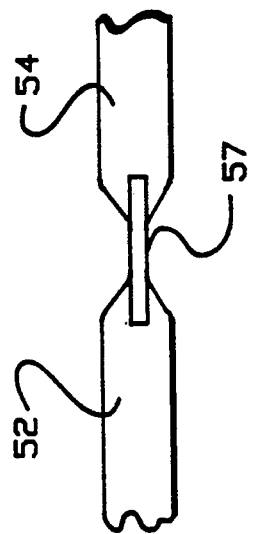
FIG. 2a is a modification of the embodiment shown in FIG. 2.

As may be clearly recognized, the living hinge 50 does not necessarily have to be constructed of a unitary piece. For example, FIG. 2a illustrates an alternative embodiment of the living hinge 50 wherein the flexible section 56 is a shim joint 57. The shim 57, which is a separate item, is secured to the first end 52 and the second end 54. Similar to the embodiment illustrated in FIG. 2, this alternative embodiment may also be manufactured using low cost materials such as flexible plastic. The embodiment illustrated in FIG. 2a may be used if it is desired to use different material for the shim joint 57 than the materials used for the ends 52, 54. Such a design may be advantageous if it is desired to use a very rigid material for ends 52 and 54 and a more flexible material for the shim joint 57.

Additional variations on the living hinge design are conceivable. For example, FIG. 2b illustrates a living hinge using a shim formed out of the first end 52. Such a design may be advantageous in adapting to the specific assembly techniques utilized by a particular manufacturer.

FIG. 3 illustrates another embodiment of the fiber diverter probe 10. In this embodiment, the wire 58 is eliminated by utilizing the aspirating or irrigating tube 70 as means for diverting the second end 54 in response to sliding the adjustable button 20. Unlike previous designs wherein the irrigating or aspirating tube is rigidly secured within the elongated member 12, the embodiment illustrated in FIG. 3 provides for the irrigating or aspirating tube 70 to be slidably mounted within the elongated member 12 in order to enable the tube 70 to divert the second end 54 in response to sliding the adjustable button 20. This design enables the aspirating or irrigating tube 70 to function as means for translating the motion of the adjustable button 20 to the fiber guide 16 in order to divert the end portion of the optical fiber, in addition to transferring air and liquid through the probe 10. This embodiment further decreases the number of separate components in the overall design of the fiber diverter probe 10, thereby reducing the cost, weight, and risk of mechanical failure of the instrument.

In this embodiment the tube 70 should be constructed of a material which is flexible but also stiff enough to effectively divert the second end 54 by a sliding motion of the tube 70. Although the illustrated embodiment shows a separate nozzle 74 which is connected to the tube 70, it may be desirable to eliminate the nozzle 74 and have the tube 70 extend to the extreme distal end of the probe 10 in order to eliminate the nozzle 74. Such a design is shown in FIG. 3a. Also illustrated in both FIGS. 3 and 3a is the fiber optic 72 for communicating laser energy from the proximal end 14 to the fiber guide 16 of the probe 10.

FIG. 3b illustrates a cross-sectional view of the handle 18 shown in FIG. 1, wherein the internal design of the handle 18 is configured to support the embodiment discussed in reference to FIGS. 3 and 3a. In this embodiment the tube 70 is shown to be connected to a shaft 90 of the adjustable button 20, thereby enabling the tube 70 to divert the second end 54 in response to sliding the button 20.

Figure 4:
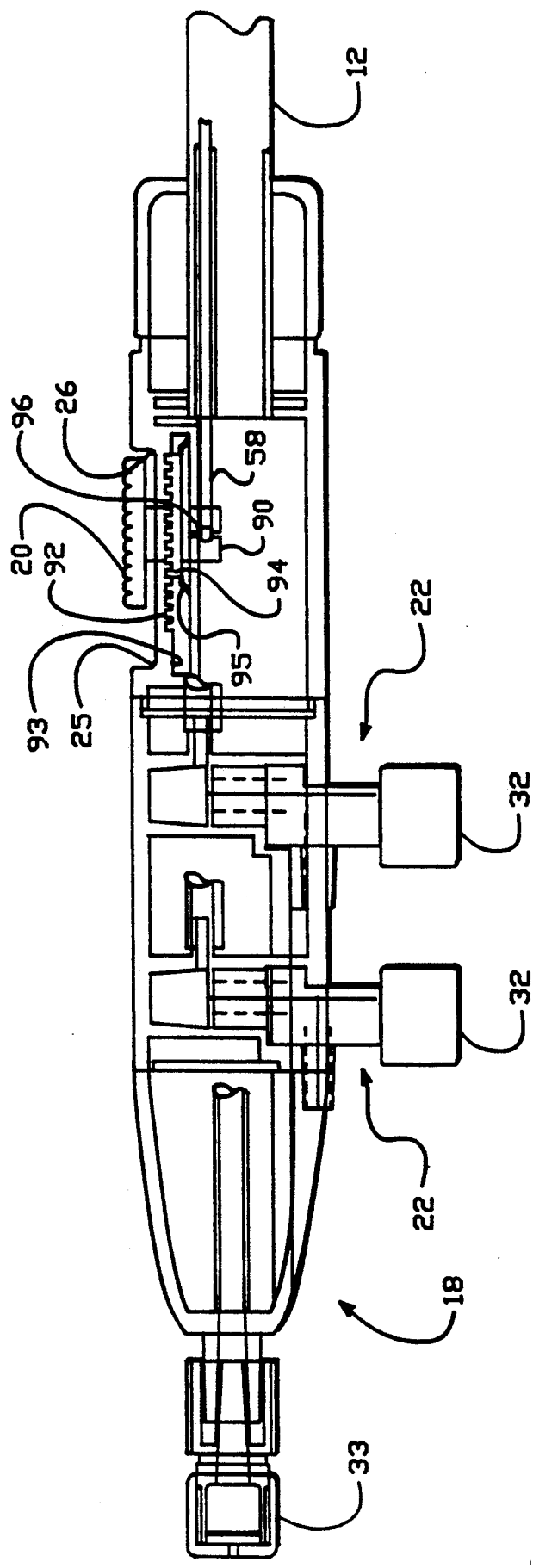
FIG. 4 is a cross-sectional view of a fiber diverter probe handle configured in accordance with the present invention.

FIG. 4 illustrates a cross-sectional view of the handle 18 showing means for locking the adjustable button 20 in a desired sliding position. The locking means includes an upper linear gear 92 on an inner wall 93 of the handle 18. The button 20 includes a shaft 90 that extends perpendicularly into the handle 18. A lower linear gear 94, that is secured to the shaft 90 of the button 20, has a plurality of cogs that interlock with the cogs of the upper linear gear 92 when the button 20 is in an non-depressed position, as illustrated in FIG. 4. The button 20 is urged into the non-depressed position by a leaf spring 95.

As can be seen in FIG. 4, the button 20 is locked into position by interlocking cogs of gears 92 and 94 when the button 20 is in the non-depressed position. However, when the button 20 is moved into the depressed position by an external force, such as a finger pressing on the button 20, the leaf spring 95 is compressed and the gear 94 is pushed away from gear 92, thus unlocking the opposing cogs of gears 92 and 94 and enabling the button 20 to sliding freely between the distal sliding position 26 and the proximal sliding position 25.

One end of the wire 58 is secured to the shaft 90, preferably by a pivot joint 96, in order to provided means for diverting the second end 54 of the hinge 50 in response to sliding the button 20.

Figure 5:
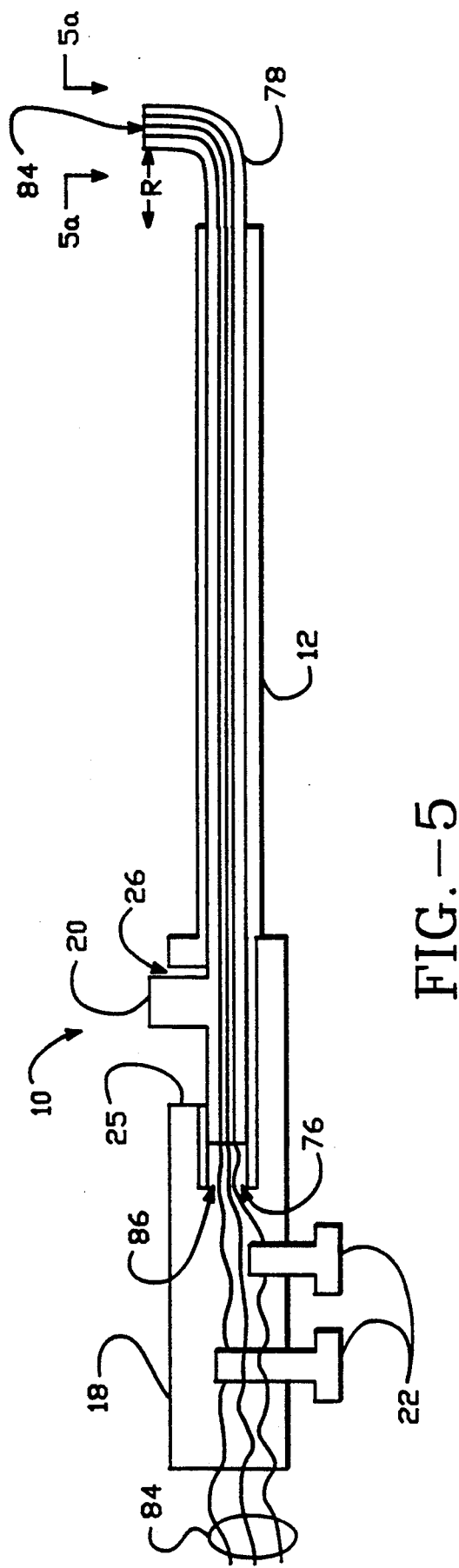
FIG. 5 is another embodiment of a fiber diverter probe configured in accordance with the present invention.
Figure 5A:
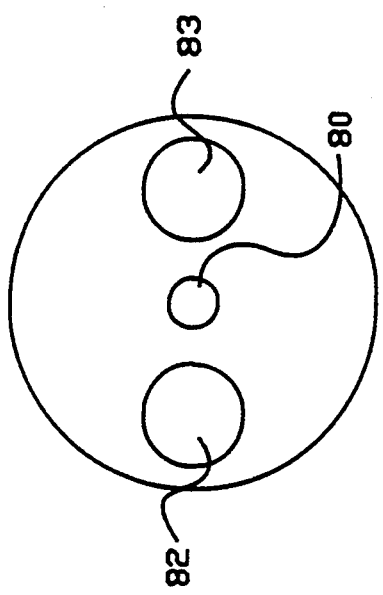
FIG. 5a is an end view of the probe shown in a taken along line 5a—5a of FIG. 5.

Referring now to FIG. 5, another embodiment of the present invention is illustrated that completely eliminates the necessity for a hinge joint in the fiber guide 16 of the fiber diverter probe 10. In this embodiment the elongated member 12 includes a central lumen 76 that contains a flexible member 78. The flexible member 78 includes at least a first lumen 80 for housing a fiber optic. The flexible member 78, which may be constructed of a thermoplastic material, may also contain additional lumens 82 and 83 for irrigating and aspirating functions (FIG. 5a). A distal end 84 of the flexible member 78 is molded to form a curve having a predetermined radius R in an unrestricted state. When the slide button 20 is in the proximal position 25, the distal end 84 of the flexible member 78 is withdrawn inside the elongated member 12 causing the entire length of the flexible member 78 to straighten out and become linear. As the adjustable button 20 is slid towards the distal position 26, the distal end 84 is pushed out of the elongated member 12 which allows the preformed shape of the flexible member 78 to achieve a predetermined curve having a radius R as shown in FIG. 5. In this manner, a fiber diverter probe is provided without the need of a hinge joint in the fiber guide 16, thus further decreasing the number of components in the design.

FIG. 5a illustrates a cross-section of the distal end 84 shown in FIG. 5. As can be seen in FIG. 5a, the flexible member 78 can include a plurality of lumens. Preferably, these lumens would include a fiber optic lumen 80 for housing the fiber optic, and aspirating and irrigating lumens 82, 83 for cleaning procedures.

The handle 18 of the probe 10 shown in FIG. 5 also includes trumpet valves 22 for regulating the flow through the lumens 82, 83. As shown in FIG. 5, line/-tubes 84, which may include an optic fiber, are inputted directly into a proximal end 86 of the flexible member 78. The handle 18, the trumpet valves 22 and the slide button 20 may all be constructed of an inexpensive thermoplastic material, thus reducing the weight and overall cost of the probe 10. By constructing the probe 10 of these materials the feasibility of a disposable probe is made possible while also reducing the overall weight of the instrument.

Although it is difficult to determine the exact weight reduction provided by the present invention due to the varying weights of probes, a fair estimate is possible. For example, a conventional, non-disposable fiber diverter probe having a single channel (for the fiber optic) typically has a mass of about 60 grams, and a three channel probe (fiber optic, aspiration, and irrigation) typically has a mass of about 98 grams. A disposable, one channel fiber diverter laser probe provided by the present invention has an estimated mass of about 45 grams and a three channel probe has an estimated mass of about 62 grams. As can be readily determined, an improved probe having additional features can be provided by the present invention at a reduced mass approaching 40%. Such a significant weight reduction is an attractive feature to surgeons who must manually hold a probe in position for long periods of time during a surgical operation.

From the above disclosure, a lightweight, low cost, less complex fiber diverter probe is provided. The reduced cost and reduced component design aspects provided by the present invention make a disposable (one time use) probe feasible to both hospitals and lone practitioners. Furthermore, the reduced mass (or weight) aspect offered by the present invention provides a very desirable comfort feature to surgeons who use fiber diverter probes.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A surgical probe, comprising:
   a flexible, elongated member having a first proximal end, a first distal end and a first passage through which an optical fiber having an end portion can be passed, said first distal end tending to form a curve when unrestricted;
   a rigid, elongated member having a second proximal end, a second distal end and a second passage through which the flexible, elongated member can be passed;
   an adjustable member secured near the first proximal end of said flexible, elongated member so that said flexible, elongated member slides within said second passage in response to movement of the adjustable member;
   said adjustable member being movable between a first position and a second position, wherein the first distal end of said flexible, elongated member is substantially enclosed within the second passage and unable to form a curve when the adjustable member is in the first position, and as the adjustable member is slid to the second position the first distal end is partially slid out of the second passage and able to form a curve in order to deflect the end portion of the optical fiber to establish an angle of deflection.

2. The surgical probe defined in claim 1, wherein said probe is designed for one-time use and at least one component of the fiber guide comprises a material that degrades at high temperatures necessary for heat sterilization.

3. The surgical probe defined in claim 1, wherein the flexible, elongated member allows for at least one lumen, said lumen communicating fluid between the first proximal end and the first distal end, said lumen further having an end portion that is deflected by the first distal end of the flexible, elongated member to establish an angle of deflection.

4. The surgical probe defined in claim 1, further comprising means for locking said adjustable member at a desired position.

5. A surgical probe, comprising:
   a rigid, elongated member having a proximal end, a distal end, a longitudinal axis and a passage through which an optical fiber having an end portion can be passed;
   a fiber guide comprising a unitary component connected near the distal end of the elongated member, said unitary component including a means for receiving the end portion of the optical fiber and means for deflecting the end portion of the optical fiber to establish a an angle of deflection;
   a handle;
   means for coupling the handle with the elongated member near the proximal end, while allowing for rotation of the elongated member and the fiber guide about the longitudinal axis while the handle remains stationary;
   translating means, having an adjustable member coupled to said handle, for translating motion of the adjustable member to the fiber guide to control the angle of deflection of the end portion of the optical fiber;
   means, coupled with the translating means, for locking the translating means to set the angle of deflection;
   at least one component of the fiber guide comprising material that degrades at high temperatures necessary for heat sterilization.

6. A surgical probe, comprising:
   a rigid, elongated member having a proximal end, a distal end, a longitudinal axis and a passage through which an optical fiber having an end portion can be passed;
   a fiber guide connected near the distal end of the elongated member, comprising means for receiving the end portion of the optical fiber and means for deflecting the end portion of the optical fiber to establish an angle of deflection;
   a handle;
   means for coupling the handle with the elongated member near the proximal end, while allowing for rotation of the elongated member and the fiber guide about the longitudinal axis while the handle remains stationary; and
   translating means, having an adjustable member coupled to said handle, for translating motion of the adjustable member to the fiber guide to control the angle of deflection of the end portion of the optical fiber.

7. The surgical probe defined in claim 6, wherein the translating means includes a wire having one end secured to said adjustable member and another end secured to the fiber guide.

8. The surgical probe defined in claim 6 further comprising at least one lumen, housed within said passage of said rigid, elongated member, for communicating fluid between the proximal end and the fiber guide, said lumen further having an end portion that is deflected by the fiber guide to establish an angle of deflection.

9. A disposable surgical probe, comprising:
   a rigid, elongated member having a proximal end, a distal end and a passage through which an optical fiber having an end portion can be passed;
   a fiber guide, connected near the distal end of the elongated member, comprising means for receiving the end portion of the optical fiber and means for deflecting the end portion of the optical fiber to establish an angle of deflection;
   translating means, having an adjustable member secured near the proximal end, for translating motion of the adjustable member to the fiber guide to control the angle of deflection of the end portion of the optical fiber;
   at least one lumen, housed within said passage of said rigid, elongated member, for communicating fluid between the proximal end and the fiber guide, said lumen further having an end portion that is deflected by the fiber guide to establish an angle of deflection; and
   at least one component of the fiber guide comprising material that degrades at high temperatures necessary for heat sterilization.

10. The surgical probed defined in claim 9, wherein said probe has a mass of less than 50 grams.

11. The surgical probe defined in claim 9, wherein the translating means includes a wire having one end secured to said adjustable member and another end secured to the fiber guide.

12. A surgical probe, comprising:
a rigid, elongated member having a proximal end, a distal end and a passage through which an optical fiber having an end portion can be passed;
a fiber guide, connected near the distal end of the elongated member, comprising means for receiving the end portion of the optical fiber and means for deflecting the end portion of the optical fiber to establish an angle of deflection;
translating means, having an adjustable member secured near the proximal end, for translating motion of the adjustable member to the fiber guide to control the angle of deflection of the end portion of the optical fiber, said adjustable member comprising a slidable button having a depressed position and a non-depressed position; and
means, coupled with the translating means, for locking the translating means to set the angle of deflection, said means for locking locks the slidable button at a desired slidable position when the button is in a non-depressed position, and releases the slidable button to slide freely when the button is depressed to the depressed position by an external force.

13. The surgical probe defined in claim 12, wherein said means for locking the translating means includes opposing linear gears having cogs that interlock when the button is in the non-depressed position.

14. The surgical probe defined in claim 12, wherein the translating means includes a wire having one end secured to said adjustable member and another end secured to the fiber guide.

15. The surgical probe defined in claim 12 further comprising at least one lumen, housed within said passage of said rigid, elongated member, for communicating fluid between the proximal end and the fiber guide, said lumen further having an end portion that is deflected by the fiber guide to establish an angle of deflection.

16. A surgical probe, comprising:
a rigid, elongated member having a proximal end, a distal end and a plurality of lumens having respective end portions;
a fiber guide, connected near the distal end of the elongated member, comprising means for receiving the end portions of the plurality of lumens and means for deflecting the end portions of the plurality of lumens to establish an angle of deflection;
an adjustable member secured near the proximal end;
means for connecting at least one of the plurality of lumens to the adjustable member and to the fiber guide, so that said at least one of the plurality of lumens translates motion of the adjustable member to the fiber guide to control the angle of deflection of the end portions of the plurality of lumens.

17. The surgical probe defined in claim 16, wherein the fiber guide consists of a unitary component.

18. The surgical probe defined in claim 16, further comprising means for locking said adjustable member at a desired position.

19. The surgical probe defined in claim 16, wherein the probe is designed for one-time use and at least one component of the fiber guide comprises a material that degrades at high temperatures.

20. A surgical probe, comprising:
a rigid, elongated member having a proximal end, a distal end and a passage through which an optical fiber having an end portion can be passed;
a fiber guide comprising a unitary component, said unitary component includes a first end that is secured to the distal end of the elongated member, a second end that receives the optical fiber, and a flexible middle section between the first and second ends, wherein flexing the middle section causes the second end to deflect the end portion of the optical fiber to establish an angle of deflection; and
translating means, having an adjustable member secured near the proximal end, for translating motion of the adjustable member to the second end of the unitary component to control the angle of deflection of the end portion of the optical fiber.

21. The surgical probe defined in claim 20, wherein at least the fiber guide comprises a material that degrades at high temperatures necessary for heat sterilization.

22. The surgical probe defined in claim 20, wherein the fiber guide is constructed of a thermoplastic material.

23. The surgical probe defined in claim 20, wherein the translating means includes a wire having one end secured to said adjustable member and another end secured to the fiber guide.

24. The surgical probe defined in claim 20 further comprising at least one lumen, housed within said passage of said rigid, elongated member, for communicating fluid between the proximal end and the fiber guide, said lumen further having an end portion that is deflected by the fiber guide to establish an angle of deflection.

25. The surgical probe defined in claim 20 wherein the unitary component comprises a living hinge.

* * * * *